United States Patent [19]

Cohen et al.

[11] Patent Number: 5,531,727
[45] Date of Patent: * Jul. 2, 1996

[54] FLUID ABSORBING ARTICLE UTILIZING A FLOW CONTROL COVER SHEET

[75] Inventors: Richmond R. Cohen, Hockessin, Del.; Edward J. Engle, Conyers, Ga.

[73] Assignee: Hercules Incorporated, Wilmington, Del.

[*] Notice: The portion of the term of this patent subsequent to Nov. 2, 2010, has been disclaimed.

[21] Appl. No.: 328,938

[22] Filed: Oct. 25, 1994

Related U.S. Application Data

[63] Continuation of Ser. No. 82,687, Jun. 25, 1993, abandoned, which is a continuation of Ser. No. 964,483, Oct. 21, 1992, Pat. No. 5,257,982, which is a continuation of Ser. No. 633,907, Dec. 26, 1990, abandoned.

[51] Int. Cl.$^6$ .............................. A61F 13/15; A61F 13/20
[52] U.S. Cl. ...................... 604/378; 604/358; 604/385.1; 604/384
[58] Field of Search ...................................... 604/358, 366, 604/367, 370, 378, 379, 384, 385.1

[56] References Cited

U.S. PATENT DOCUMENTS

| | | |
|---|---|---|
| 2,668,785 | 2/1954 | Jefferson et al. . |
| 2,751,962 | 6/1956 | Drummond . |
| 2,983,625 | 5/1961 | Schappel . |
| 3,388,028 | 6/1968 | Alexander . |
| 3,768,480 | 10/1973 | Meser et al. ............................. 604/370 |
| 3,936,555 | 2/1976 | Smith, II ................................. 428/218 |
| 4,010,752 | 3/1977 | Denny ...................................... 604/377 |
| 4,223,677 | 9/1980 | Anderson ................................ 604/365 |
| 4,397,644 | 8/1983 | Matthews et al. . |
| 4,480,000 | 10/1984 | Watanabe et al. . |
| 4,519,799 | 5/1985 | Sakurai et al. . |
| 4,560,372 | 12/1985 | Pieniak . |
| 4,627,848 | 12/1986 | Lassen et al. . |
| 4,652,484 | 3/1987 | Shiba et al . |
| 4,673,402 | 6/1987 | Weisman et al. . |
| 4,725,473 | 2/1988 | Gompel et al. . |
| 4,753,834 | 6/1988 | Braun et al. ............................. 604/366 |
| 4,755,178 | 7/1988 | Insley et al. . |
| 4,767,586 | 8/1988 | Radwanski et al. . |
| 4,781,962 | 11/1988 | Zammarripa et al. . |
| 4,798,603 | 1/1989 | Meyer et al. . |
| 4,822,668 | 4/1989 | Tanaka et al. . |
| 4,837,078 | 6/1989 | Harrington . |
| 4,842,596 | 6/1989 | Kielpikowski et al. . |
| 4,846,824 | 7/1989 | Lassen et al. . |
| 4,883,707 | 11/1989 | Newkirk .................................. 604/370 |
| 4,886,697 | 12/1989 | Perdelwitz et al. . |
| 4,892,534 | 1/1990 | Datta et al. . |
| 4,892,598 | 1/1990 | Stevens et al. . |
| 4,931,357 | 6/1990 | Marshall et al. . |
| 5,033,172 | 7/1991 | Harrington . |
| 5,045,387 | 9/1991 | Schmalz . |
| 5,057,357 | 10/1991 | Winebarger . |
| 5,221,573 | 6/1993 | Baigas, Jr. .............................. 428/218 |
| 5,257,982 | 11/1993 | Cohen et al. ............................ 604/358 |

FOREIGN PATENT DOCUMENTS

| | | |
|---|---|---|
| 0157649 | 4/1985 | European Pat. Off. . |
| 0159671 | 4/1985 | European Pat. Off. . |
| 0175481 | 8/1985 | European Pat. Off. . |
| 0210968 | 7/1986 | European Pat. Off. . |
| 0254476 | 7/1987 | European Pat. Off. . |
| 0325416 | 1/1989 | European Pat. Off. . |
| 0399511 | 5/1990 | European Pat. Off. . |
| 2087240 | 11/1981 | United Kingdom . |
| 2124907 | 8/1983 | United Kingdom . |

OTHER PUBLICATIONS

"Multilayer Diaper Coverstocks Offer New Opportunities" By James E. Smith, James River Corp., Jul. 1988.
"Multi-Layer Nonwovens For Coverstock, Medical, and Other End Uses" By Jouko Pirkkanen, President, Finnwad Ltd., Nov. 1987.

*Primary Examiner*—David H. Willse
*Assistant Examiner*—P. Zuttarelli
*Attorney, Agent, or Firm*—Mark D. Kuller; Robert P. O'Flynn O'Brien; John E. Crowe

[57] ABSTRACT

A nonwoven fabric having flow control properties suitable for use in a fluid absorbing article such as a diaper, incontinence pad, or the like; and a process for preparation thereof by utilizing unbonded carded staple fiber elements or webs having different average dpf values compiled in graduated order from high-to-low average dpf, then compressed and bonded to a desired constant fabric density.

52 Claims, 2 Drawing Sheets

FLUID ABSORBING ARTICLE UTILIZING A FLOW CONTROL COVER SHEET

This application is a continuation of application Ser. No. 08/082,687, filed Jun. 25, 1993, abandoned, which is a continuation of application Ser. No. 07/964,483, filed Oct. 21, 1992, now U.S. Pat. No. 5,257,982, which is a continuation of application Ser. No. 07/633,907, filed Dec. 26, 1990, abandoned.

The present invention relates to the efficient production and utilization of nonwoven fabric having built in fluid-control properties favoring a rapid acquisition or flow-through rate in one direction coupled with resistance to rewet or fluid flow in the opposite direction.

BACKGROUND OF THE INVENTION

It is generally recognized that success in the marketplace, particularly with respect to fluid-absorbing articles such as disposable diapers, incontinence garments or pads and the like, depends substantially on functional efficiency, including comfort of the wearer, appearance, and price of the product being sold.

In general, such product must have a fluid-retaining core component, usually compressing one or more layers of absorbent material such as wood pulp, rayon, gauze, tissue or the like, and, in some cases, synthetic hydrophilic material such as a superabsorbent powder.

To protect clothing, and surrounding areas from being stained or wetted by fluids retained in a pad or core, such article is generally backed by a fluid-impervious backing component.

The article or fluid-absorbent pad generally also has a nonwoven-type fabric or coverstock material, which defines at least the body-contacting surface of the article. Functionally speaking, the nonwoven coverstock material is intended to help control fluid flow and insulate the wearer from continuous contact with moisture already retained in the absorbent pad or core. Such facing or coverstock must be pervious to fluids on its body-contacting side so as to promote the direct and immediate transfer of each fluid application or insult (i.e. acquisition rate) to the fluid absorbent core component; the coverstock itself, however, should be essentially nonabsorbent to fluid and remain soft and dry. It is particularly important, in this regard, to minimize potential rewet or back migration of fluid from the fluid-absorbent core component, after repeated insults, and for the cover-stock to continue to feel dry and soft without serious strength loss.

It is now generally accepted that major improvements can be achieved regarding the comfort of the wearer of such articles (a) by further increasing coverstock thickness or caliper to retain a defined physical separation between a wearer's skin and the fluid-retaining core and/or (b) by improving the above-noted fluid flow control, especially flow through and back flow or rewet properties.

With respect to such properties it is noted that continued efforts are being made for the purpose of improving flow control without adversely affecting production efficiency, strength or comfort to develop products offering such advantages.

In U.S. Pat. No. 4,798,603 of Meyer et al (assigned Kimberly-Clark) absorbent articles such as diapers, incontinence garments, wound dressings and the like are proposed, in which rewet or back fluid flow from the core or absorbent component is reduced by using a liquid permeable top sheet of synthetic hydrophobic polymer filaments having an effective average pore size larger than the absorbent core, with a liquid-permeable transport layer interposed between the top sheet and the absorbent core. The transport layer, as described, is less hydrophilic than the core, has a uniform density, and an average pore size which is less than that of the bonded top sheet layer, but greater than that of the core.

U.S. Pat. No. 4,883,790 of Newkirk (assigned to James River Corporation) utilizes a high loft nonwoven coverstock having a carded fiber web of 3 dpf or greater, bonded to a carded fiber web having an average denier of 3 or less. Each layer or web, as described, contains sufficient thermoplastic bicomponent fiber to permit inter-and intra-air bonding of the layers.

U.S. Pat. No. 4,652,484 (assigned Kao Corporation) relates to nonwoven fabrics for disposable absorbent articles such as sanitary napkins, paper diapers and the like. The articles are made of hot-melt fiber having a 90°–140° C. melting range and consisting of 2 layers of sterically buckled fiber having 1–3 dpf and 1.5–6 dpf respectively.

While the art, as above described, appears to recognize and attempts to address fluid flow problems plus other known deficiencies, the art has not, thus far, been able to provide a unitary nonwoven cover sheet with an efficient fluid flow control mechanism while supplying cost and other market needs including a reduced number of conventional bonding steps.

OBJECT OF THE INVENTION

It is an object of the present invention to efficiently produce durable nonwoven coverstock material suitable for use as coverstock or the like which retains high acquisition of flow-through properties coupled with acceptable rewet properties.

DETAILED DESCRIPTION OF THE INVENTION

The above object, particularly the production of a unitary single bonded nonwoven coverstock material having fluid-flow-controlling properties is achieved by (a) carding homogeneous or mixed dpf staple fiber or filament to obtain a plurality, preferably about 2 to 5, unbonded elements or webs individually having different average dpf values within a predetermined dpf range, preferably about 1–20 dpf or higher;

(b) compiling the plurality of unbonded elements or webs in graduated sequence based on highest-to-lowest average dpf values, or the reverse, for purposes of bonding, such that the corresponding material face defined as having the highest average dpf is receivably arranged with respect to a fluid source such as the body-contacting side of the coversheet, and the opposite face, defined by an element or web having the lowest average dpf, is arranged in feedable proximity to a core component or similar fluid-retaining means; and (c) bonding the compiled element(s) or web(s) under conditions favoring a nonwoven material of desired constant density. This step is preferably, but not exclusively carried out by use of a hot calender or by a pressure bonding step and optionally preceded by passage through pressure-imparting and retaining means such as one or more sets of plain or patterned roller nip(s) to maintain a constant reproducible density within about 0.2–0.02 gm/cc and preferably within a 0.04 g/cc–0.08 g/cc range.

Where pressure or calender bonding is utilized, such rollers can usefully impart a relatively small or moderate compressive force, depending upon the resilience of the respective fiber mix in the elements or webs, the amount of crimp, and the average denier range of the elements or webs.

A nonwoven material suitable for use as coverstock is further represented in accompanying figures as schematic cut away longitudinal cross sections of steps within the instant process, in which a plurality of fiber elements or webs are represented as shaded rectangular boxes, each representing a web or element of conventionally spun, quenched, crimped, cut, and carded (homogeneous or mixed) staple fiber having different average dpf values and arranged in graduated sequence.

Figure 1:
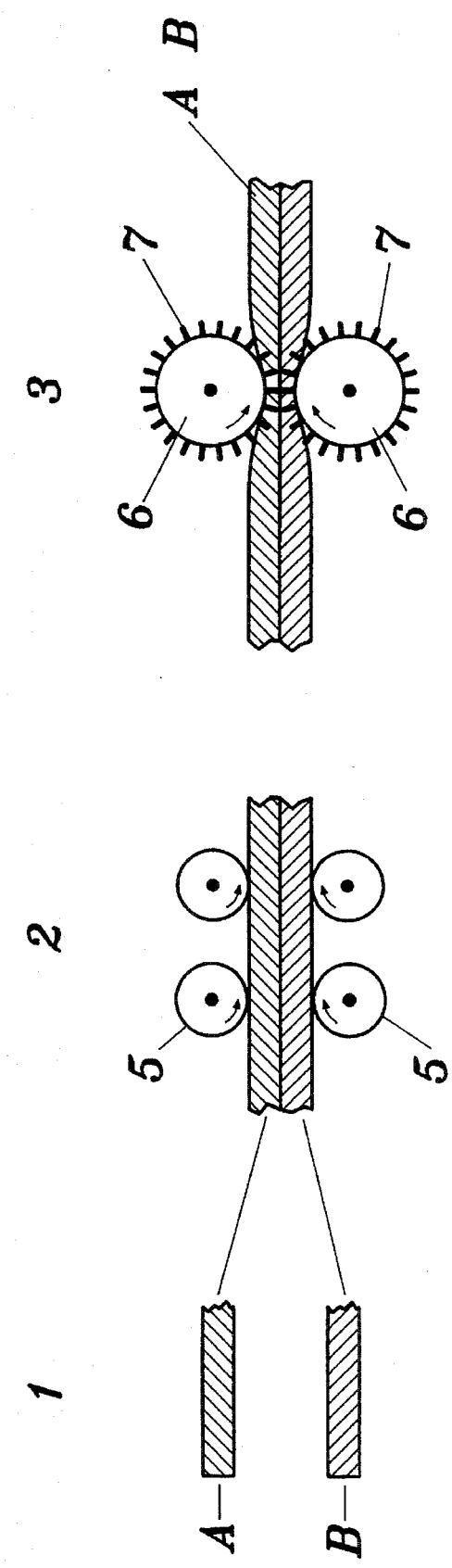
FIGS. 1 and 2 show arranging unbonded elements, compressing compiled elements using nip-adjustable rollers, and bonding using hot patterned calendar rolls having teeth.
Figure 2:
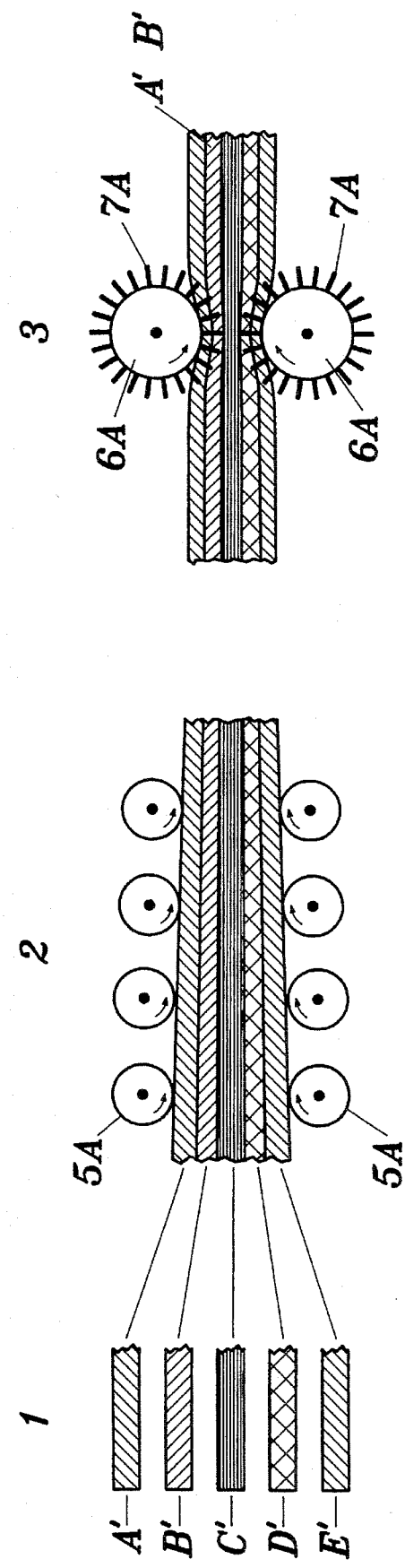

The bonded nonwoven materials (step 3 of FIGS. 1 and 2) in the above-described process are exemplified in accompanying FIGS. 1 and 2, in which components A-B and $A^1$-$E^1$ respectively represent two (2) and five (5) unbonded carded fiber elements or webs, optionally including fibrillated film in schematic longitudinal sections, each of which is obtained by conventional steps as noted above using spinnable or castable thermoplastic spun melt composition(s); the actual internal structure differences in average dpf and relative height of each element or web are not shown to scale.

For purposes of the present invention, the arrangement of element A-B in FIG. 1 is assumed to be from highest desired average dpf (e.g. A) to lowest average dpf (e.g. B) as compiled and optionally comprised. As earlier noted, however, the general choice of an acceptable degree of compression and reduction in combined carded web heights of the webs or elements (Step 2) will more or less depend upon the physical or time-wise proximity of the downstream bonding step (Step 3) to the web compiling and optional compressing steps (Step 2); (b) upon individual web resiliency or fiber crimp and resiliency; (c) upon the desired amount of loft in the resulting nonwoven coverstock; and (d) upon the type of bonding (e.g. pressure bonding, calender, laser, hot air sonic etc.) to be used.

The word "oriented" as used herein and in the claims with respect to the nonwoven coverstock in the finished absorbent article (i.e. diaper, etc.) indicates the positioning of the elements of highest average dpf on the body contacting or fluid source side of the article.

In a typical process for the nonwoven, the two unbonded elements (A and B of FIG. 1) are arranged in order of increased average dpf (Step 1), compiled (not shown) and subjected to compression (Step 2) using nip-adjustable rollers (5), then bonded (Step 3) by being fed between hot patterned calender rolls (6) in which the surface patterns are represented as teeth (7), the nip and temperature of the calender rolls being adjusted to provide a nonwoven (AB) having a desired constant density falling within the above-indicated density range.

In FIG. 2, five (5) separate elements or webs are arranged (step 1) in descending average dpf order, compiled, and gradually compressed (Step 2) by using a series of compression rolls (5A) with progressively reduced nip at a point upstream of a calender bonding station (Step 3) employing patterned calender rolls (6A), the nip of the calender rolls for such purposes being optionally from about 100%–30% of the final upstream nip of the closest set of compression roll (5A), the amount of prebonding compression again depending upon the desired constant density in the bonded and cooled nonwoven $A^1B^1$.

For convenience, the same arabic numbers denote identical or similar components within FIGS. 1 and 2.

Elements or webs used in the present invention can be conventionally prepared using either monocomponent and/ or bicomponent staple fiber spun from thermoplastic resins such as spinnable (preferably 16–20 MFR) polyolefin spun melt, polypropylene/polyester copolyester/polyester polyethylene/polypropylene, low melting polyester/polyester, polyester/polypropylene, polyethylene/polyester and the like, which are then subject to a rapid or delayed air quench, drawn (preferably 1× to 1.6× or higher), crimped (preferably 10–26 c/inch), cut (not exceeding about 3 inches and preferably about ¼ to 3 inches), carded (preferably using mixed fiber and conventional techniques) and compiled.

In order to obtain the desired elements or webs it is found convenient, for instance, to air mix staple fiber of two (or more) different dpf values and of the same or different lengths, and then card the resulting mixed fiber batches to obtain desired average dpf-elements or web. For such purpose, a plurality of fiber mixtures within a ratio of 100%–0% to 0%–100% by weight of the two desired dpf extremes or premix batches of fibers are suitable for producing elements or webs for carrying out the forming, compiling and compressing, and bonding steps.

For present purposes, fiber mixtures or fiber premixes can include fibers or filaments having different cross-sectional configurations such as circular, delta, y, x, diamond, dogbone, etc. of the same or different dpf values, and also include mixtures of different polymeric filaments, including polyamides, polyolefins, polyesters etc., the choice depending upon the desired durability, softness, strength, and opacity characteristics of the nonwoven.

Additives and techniques for their use in spinning, quenching, crimping, cutting, and carding operations, including choice and application of lubricants, antistatic agents, antioxidants, wetting agents, etc. known in the art are includable, within the scope of the present invention.

Looking further to the process and resulting product, we find that compression step (Step 2) of FIGS. 1 and 2 can be conveniently achieved adjusted to all within desired density ranges by passage of elements or webs from carding- and web-forming steps through one or more patterned or plain pressure rolls which can be manually or automatically adjusted, nip-wise, to consistently obtain and maintain about the same % compression based on the original weight and measured height of the carded webs, assuming a consistent, but not necessarily equal, weight for each individual element throughout the process steps; where use of binders, antioxidants, antistatic agents, etc. may vary web weight and resiliency. The nip size and positioning of upstream pressure rolls prior to bonding must be adjusted so as to minimize uneven expansion and preserve a consistent relative density (i.e. g/volume) in the resulting relaxed bonded nonwoven material.

The compiling step (Step 1) requires arrangement of compressed elements or webs in graduated sequence by average dpf, as above noted, arranging the webs according to the relative percent by weight of high dpf fiber or filament utilized in the carding operation. Such webs or elements may all be compiled in a machine direction or, if desired, arranged at various angles to the machine direction to provide additional strength consistent with retention of good moisture transmittal and capillary resistance to rewet.

If desired the compiled and compressed unbonded fiber-containing elements or webs may also include one or more layers of fibrillated film, the fibrillation step being generally consistent in apparent dpf value to the graduated sequence of adjacent spun fiber- or filament-containing elements or webs, and conveniently cast from a similar-type thermoplastic polymer.

The bonding step, (3) of both FIGS. 1 and 2, can optionally utilize alternative bonding techniques such as needle punch, thermal, laser or sonic bonding techniques, provided the resulting nonwoven falls generally within a range of about 10–35 gm/yd$^2$ and preferably 15–30 g/yd$^2$ and consistent density values within the above-indicated g/cc range can be maintained.

Nonwoven material, as above described, can be readily utilized as coverstock for multi-layered hygiene products such as diapers, sanitary napkins and the like in the manner produced and described, for instance, in U.S. Pat. Nos. 4,112,153, 4,391,869, 4,573,987, 4,578,066 and 4,798,757.

The following examples and Table further illustrate, but do not limit the scope of the present invention.

EXAMPLE I

A) A test bale of round crimped isotactic Polypropylene 15 dpf staple is prepared from corresponding degraded spun melt (MFR 20 dg/min) fed through a 1½" extruder and 210 hole spinnerette at 285° C.; air quenched[*1], and passed at constant speed, over a feed or kiss roll partly immersed in a tank of Lurol PP-912[*2] as an antistatic agent and lubricant (estimated 0.4% by wt.), drawn to 1.5×, crimped (at 20/inch), and cut as 1.5 inch staple. The resulting homogeneous staple is then baled as "Test A Bale".

[*1] at room temeperture
[*2] A neutralized phosphoric acid/alcohl ester obtained commercially from G. A. Goulston Incorporated B) A test bale of round cross section 3 dpf polypropylene staple is prepared identically to Test A bale (supra) and baled as "Test B Bale."

C) A test bale of round cross section 20 dpf of polypropylene staple is prepared identically to Test A bale (supra) and baled as "Test C Bale."

D) A test bale of delta cross section 3 dpf polypropylene staple is prepared as A (supra) and baled as "Test D Bale."

E) A test bale of round cross section polyethylene/polypropylene sheath/core bicomponent staple is passed through a conventional spin pack at a temperature of 280° C., air quenched, crimped, cut and baled as in Test E Bale.

Testing Procedures (a) Fluid Acquisition Test of the compiled and bonded test nonwovens is determined by pressure-driven GATS (Gravimetric Absorbency Testing System) using GATS II test equipment[*3] having a single point source for evaluating the capacity of absorbent samples[*5] For test purposes the core or fluid storage component is represented by a mixture of cellulose, Pulpex® E338[*4] and superabsorbent powder having a density of about 0.08 E/cc and a basis weight of about 300 gm/m$^2$[*6].

[*3] Commercially obtainable from M/K Systems Inc. of Danvers, Mass.
[*4] A product of Hercules Incorporated
[*5] incoming flow rate at 10.7 ml/sec (unimpeded), one second
[*6] thermally bonded core (b) Rewet Properties of the test nonwovens are determined by achieving an 80% saturating of a core or the fluid storage component through the test nonwoven, utilizing a dilute saline solution plus sufficient surfactant to obtain a surface tension of about 53 dyne/cm. After 5 minutes the test material is placed over the wet core and covered with a dry bonded core and pressed to 0.5 psi for 2 minutes. The gain in weight of the dry core is reported as rewet in grams.

EXAMPLE II

A. A constant density variable pore-size nonwoven is prepared in-line consisting of two 15 gm/yd$^2$ webs prepared respectively by opening and carding equal weights of Test A Bale and Test B Bale .(supra), compiling the resulting webs in machine direction and calender bonded, using a quilted bond-patterned calender of slightly smaller nip at 165° C. to obtain nonwoven test material (TM 1) of 30 gm/yd$^2$ having a density of 0.06 gm/cc (compressed). The resulting test material is subject to the above-described Fluid Acquisition Test (described above), mounting the 15 dpf web facing on the liquid source side and the 3 dpf web on the liquid absorbent (core) side for testing purposes. The liquid uptake in ml/second is reported as T-1 in Table I below.

B. Example II A. is repeated with the TM 1 test material mounted in reverse order (i.e. 15 dpf web on core side) and the Fluid Acquisition Test repeated. The liquid uptake in ml/second is reported in Table I below as sample T-2.

C. Two 3 dpf webs identical to II B are prepared using the Test B Bale, compressed to ½ compiled web height and bonded in the manner of II A supra for use as a control. Test results are reported in Table I as C-1.

EXAMPLE III

A. A comparable constant density variable pore-size nonwoven is made (not in line) using carded 15 dpf and 3 dpf webs from Test A and Test B Bales, each of 13 gm/yd$^2$. The compiled webs are arranged in machine direction and calender bonded at constant density as in Example II A., and the resulting nonwoven test material mounted in the same positions as reported in EX II A. and B. (i.e. 15 dpf/3 dpf and 3 dpf/15 dpf positions respectively) and tested for Fluid Acquisition and Rewet rates as above described. Test results are reported in Table I as tests T-3 and T-4.

B. A control consisting of two 13 gm/yd$^2$ 3 dpf webs using Test B Bale fiber is otherwise identically prepared, tested and reported in Table I as C-2.

TABLE I

| Test Sample | dpf Arrangement | Acquisition Rate (ml/second) | Rewet (gm) | Density (g/CC compressed) |
|---|---|---|---|---|
| T-1[*1] | 15/3 | 8.1 | — | .06 |
| T-2 | 3/15 | 7.7 | — | .06 |
| C-1 | 3/3 | 7.2 | — | .06 |
| T-3[*1] | 15/3 | 8.2 | 0.31 | .05 |
| T-4 | 3/15 | 6.8 | 0.37 | .05 |
| C-2 | 3/3 | 7.2 | 0.36 | .05 |

[*1] high average dpf facing oncoming liquid

EXAMPLE IV

Comparable test materials obtained as in Example II and III but using 20 dpf/3 dpf arrangements of webs from fiber of Test Bale C and Test Bale D of Example I are used to produce test material of comparable acquisition and rewet characteristics and slightly more opaque appearance than TM-1 for Example II.

EXAMPLE V

Comparable test materials obtained in the manner of Example II and III but using 15 dpf/3 dpf and 3 dpf/15 dpf mountings of nonwovens obtained using webs of Test Bales A and D of Example I are used to produce test material of comparable acquisition and rewet characteristics with more opacity than found in TM-1 or TM-2 of Example II.

EXAMPLE VI

Comparable test materials obtained as in Examples II–III but using 6 dpf (Test E Bale round bicomponent) and 3 dpf Test B Bale round monocomponent fiber webs (6 dpf/3 dpf) produce test materials of generally comparable acquisition and rewet rates to those obtained in Example II.

What we claim and protect by Letters Patent is:

1. A fluid-absorbing article comprising, in combination, a nonwoven coverstock component having fluid flow-controlling properties, a fluid-retaining core component, and a fluid impervious backing component, the core component being located between the coverstock and the backing components, the coverstock component having a generally constant density in a range of 0.2 g/cc to 0.02 g/cc and comprising an oriented nonwoven material comprised of at least two layers, each of the layers being layered in a predetermined sequence, compressed together and bonded together, the layers comprising:

(a) a first exterior layer having a first average denier per filament value, the first exterior layer being comprised of at least one filament; and (b) a second interior layer adjacent the first exterior layer and having a second average denier per filament value lower than the first average denier per filament value, the second interior layer being comprised of at least one filament.

2. A coverstock component having a generally constant density in a range of 0.2 g/cc to 0.02 g/cc and comprising an oriented nonwoven material comprised of at least two layers, each of the layers being layered in a predetermined sequence, compressed together and bonded together, the layers comprising:

(a) a first exterior layer having a first average denier per filament value, the first exterior layer being comprised of at least one filament; and (b) a second interior layer adjacent the first exterior layer and having a second average denier per filament value lower than the first average denier per filament value, the second interior layer being comprised of at least one filament.

3. A fluid-absorbing article comprising, in combination, a nonwoven coverstock component having fluid flow-controlling properties, a fluid-retaining core component, and a fluid impervious backing component, the core component being located between the coverstock and the backing components, the coverstock component having a density in a range of 0.2 g/cc to 0.02 g/cc and comprising an oriented nonwoven material comprised of at least two layers having a generally constant density, each of the layers being layered in a predetermined sequence, compressed together and bonded together, the layers comprising:

(a) a first exterior layer having a first average denier per filament value, the first exterior layer being comprised of at least one carded staple fiber or filament; and (b) a second interior layer adjacent the first exterior layer and having a second average denier per filament value lower than the first average denier per filament value, the second interior layer being comprised of at least one carded staple fiber or filament.

4. The fluid absorbing article of claim 3 wherein the coverstock component has a generally constant density in the range of 0.04 g/cc to 0.08 g/cc.

5. The fluid-absorbing article of claim 3 wherein the first exterior layer comprises at least two staple fibers or filaments each having a different denier value.

6. The fluid-absorbing article of claim 3 wherein the second interior layer consists essentially of at least one carded staple fiber or filament.

7. The fluid-absorbing article of claim 3 wherein the second interior layer comprises at least two staple fibers or filaments each having a different denier value.

8. The fluid-absorbing article of claim 3 wherein the average dpf values of the respective layers of the coverstock material fall within a range of about 1–20 dpf.

9. The fluid-absorbing article of claim 3 wherein the first exterior layer consists essentially of one carded staple fiber or filament.

10. The fluid-absorbing article of claim 9 wherein the second interior layer consists essentially of at least one carded staple fiber or filament.

11. The fluid-absorbing article of claim 9 wherein the second interior layer comprises at least two staple fibers or filaments each having a different denier value.

12. The coverstock material of claim 3 wherein the layers additionally comprise a third layer adjacent the second layer, the third layer having a third average denier per filament value lower than the second average denier per filament value, the third layer being comprised of at least one carded staple fiber or filament.

13. The coverstock material of claim 12 wherein the third layer consists essentially of at least one carded staple fiber or filament.

14. The coverstock material of claim 12 wherein the third layer comprises at least two staple fibers or filaments each having a different denier value.

15. The coverstock material of claim 12 wherein the layers additionally comprise a fourth layer adjacent the third layer, the fourth layer having a fourth average denier per filament value lower than the third average denier per filament value, the fourth layer being comprised of at least one carded staple fiber or filament.

16. The coverstock material of claim 15 wherein the fourth layer consists essentially of at least one carded staple fiber or filament.

17. The coverstock material of claim 15 wherein the fourth layer comprises at least two staple fibers or filaments each having a different denier value.

18. The coverstock material of claim 15 wherein the layers additionally comprise a fifth layer adjacent the fourth layer, the fifth layer having a fifth average denier per filament value lower than the fourth average denier per filament value, the fourth layer being comprised of at least one carded staple fiber or filament.

19. The coverstock material of claim 18 wherein the fifth layer consists essentially of at least one carded staple fiber or filament.

20. The coverstock material of claim 18 wherein the fifth layer comprises at least two staple fibers or filaments each having a different denier value.

21. A nonwoven coverstock material having a density in the range of approximately 0.2 g/cc to 0.02 g/cc and exhibiting fluid-flow controlling properties, comprised of at least two respective layers having a generally constant density, each of the layers being layered in a predetermined sequence, compressed together and bonded together, the layers comprising:

(a) a first layer having a first average denier per filament value, the first exterior layer being comprised of at least one carded staple fiber or filament; and (b) a second layer adjacent the first exterior layer and having a second average denier per filament value lower than the first average denier per filament value, the second interior layer being comprised of at least one carded staple fiber or filament.

22. The coverstock of claim 21 wherein one or more of the layers comprise a fibrillated film.

23. The nonwoven coverstock material of claim 21 wherein coverstock component has a generally constant density in the range of 0.04 g/cc to 0.08 g/cc.

24. The coverstock material of claim 21 wherein the first exterior layer comprises at least two staple fibers or filaments each having a different denier value.

25. The coverstock material of claim 21 wherein the second interior layer consists essentially of at least one carded staple fiber or filament.

26. The coverstock material of claim 21 wherein the second interior layer comprises at least two staple fibers or filaments each having a different denier value.

27. The coverstock material of claim 21 wherein the first exterior layer consists essentially of one carded staple fiber or filament.

28. The coverstock material of claim 27 wherein the second interior layer consists essentially of at least one carded staple fiber or filament.

29. The coverstock material of claim 27 wherein the second interior layer comprises of at least two staple fibers or filaments each having a different denier value.

30. The coverstock material of claim 21 wherein the layers additionally comprise a third layer adjacent the second layer, the third layer having a third average denier per filament value lower than the second average denier per filament value, the third layer being comprised of at least one carded staple fiber or filament.

31. The coverstock material of claim 30 wherein the third layer consists essentially of at least one carded staple fiber or filament.

32. The coverstock material of claim 30 wherein the third layer comprises at least two staple fibers or filaments each having a different denier value.

33. The coverstock material of claim 30 wherein the layers additionally comprise a fourth layer adjacent the third layer, the fourth layer having a fourth average denier per filament value lower than the third average denier per filament value, the fourth layer being comprised of at least one carded staple fiber or filament.

34. The coverstock material of claim 33 wherein the fourth layer consists essentially of at least one carded staple fiber or filament.

35. The coverstock material of claim 33 wherein the fourth layer comprises at least two staple fibers or filaments each having a different denier value.

36. The coverstock material of claim 33 wherein the layers additionally comprise a fifth layer adjacent the fourth layer, the fifth layer having a fifth average denier per filament value lower than the fourth average denier per filament value, the fifth layer being comprised of at least one carded staple fiber or filament.

37. The coverstock material of claim 36 wherein the fifth layer consists essentially of at least one carded staple fiber or filament.

38. The coverstock material of claim 36 wherein the fifth layer comprises at least two staple fibers or filaments each having a different denier value.

39. The coverstock material of claim 21 wherein the average dpf values of the respective layers fall within a range of about 1–20 dpf.

40. The coverstock material of claim 39 wherein about 2–5 unbonded layers are compiled and then calender bonded to obtain the nonwoven coverstock material.

41. The coverstock material of claim 39 wherein about 2–5 layers are compiled and then through air bonded to obtain the nonwoven coverstock material.

42. The coverstock material of claim 39 wherein about 2–5 layers are compiled and then laser bonded to obtain the nonwoven coverstock material.

43. The coverstock material of claim 39 wherein about 2–5 layers are compiled and then sonic bonded to obtain the nonwoven coverstock material.

44. The coverstock material of claim 39 wherein the respective layers comprise polypropylene monocomponent staple and/or polyethylene sheathed bicomponent staple not exceeding about 3 inches in length.

45. The coverstock material of claim 39 wherein the coverstock component comprises layers of staple fiber having a cross section selected from at least one of a round, delta, diamond, Y, X, or dog bone-type configuration.

46. The coverstock material of claim 39 wherein one or more of the respective layers comprise carded thermoplastic-monocomponent and/or—bicomponent staple.

47. The coverstock material of claim 46 wherein the respective layers comprise carded polypropylene-staple and/or sheathed bicomponent-staple selected from polyethylene/polypropylene, low melting polyester/polyester, polyester/polypropylene and polyethylene/polyester fiber.

48. The coverstock material of claim 39 wherein one or more of the compiled layers comprise carded thermoplastic-monocomponent and/or -bicomponent staple.

49. The coverstock material of claim 48 wherein about 2–5 unbonded layers are compiled and then calender bonded to obtain the nonwoven coverstock material.

50. The coverstock material of claim 49 wherein the compiled layers comprise carded polypropylene-staple and/or sheathed bicomponent-staple selected from polyethylene/polypropylene, low melting polyester/polyester, polyester/polypropylene and polyethylene/polyester fiber.

51. The coverstock material of claim 50 wherein the complied layers comprise polypropylene monocomponent staple and/or polyethylene sheathed bicomponent staple not exceeding about 3 inches in length.

52. The coverstock material of claim 51 wherein coverstock component has a generally constant density in the range of 0.04 g/cc to 0.08 g/cc.

* * * * *